United States Patent

DuPont

Patent Number: 5,843,045
Date of Patent: Dec. 1, 1998

[54] INFUSION ILLUMINATOR

[76] Inventor: Frank Stuart DuPont, 4495 Clarke Dr., East China, Mich. 48054

[21] Appl. No.: 785,180

[22] Filed: Jan. 17, 1997

[51] Int. Cl.⁶ ..................................................... A61M 5/00
[52] U.S. Cl. ............................................................ 604/251
[58] Field of Search ............................. 604/246, 251–255

[56] References Cited

U.S. PATENT DOCUMENTS

| Re. 32,294 | 11/1986 | Knute | 604/253 |
|---|---|---|---|
| 3,217,709 | 11/1965 | Schneider et al. | 604/251 |
| 3,563,090 | 2/1971 | Deltour | 73/194 |
| 3,641,543 | 2/1972 | Rigby | 340/239 R |
| 4,498,901 | 2/1985 | Finch | 604/65 |
| 4,673,397 | 6/1987 | Lynn et al. | 604/251 |
| 4,976,687 | 12/1990 | Martin | 604/65 |
| 5,045,069 | 9/1991 | Imparato | 604/253 |
| 5,346,466 | 9/1994 | Yerlikaya et al. | 604/253 |
| 5,690,612 | 11/1997 | Lopez et al. | 604/93 |

Primary Examiner—Wynn Wood Coggins
Assistant Examiner—Deborah Blyveis
Attorney, Agent, or Firm—Young & Basile, P.C.

[57] ABSTRACT

An I.V. apparatus including a stand, a bag hangably supported at an upper end thereof from the stand and adapted to contain an I.V. solution, a delivery tube for intravenous delivery of the I.V. solution to a patient by a catheter, a drip chamber extending downwardly at an upper end thereof from a lower end of the I.V. bag and connected at a lower end thereof with the delivery tube, a metering device positioned at the lower end of the I.V. bag and operative to deliver I.V. solution in drip fashion from the I.V. bag to the drip chamber, and an illumination device to insure that the desired drippage flow is taking place. The illumination device comprises a lamp assembly including a housing, batteries positioned within the housing, a light source positioned in the housing and powered by the batteries, a switch controlling the delivery of power from the batteries to the light source, and a clamp for releasably attaching the lamp to the upper end of the drip chamber. With the clamp releasably attached to the upper end of the drip chamber, a rod extending downwardly from the clamp positions the lamp housing in freestanding relation to the drip chamber with the light source positioned proximate to but spaced from the drip chamber so that the light source is operative to illuminate the drip chamber and thereby verify the presence of a drippage flow.

7 Claims, 2 Drawing Sheets

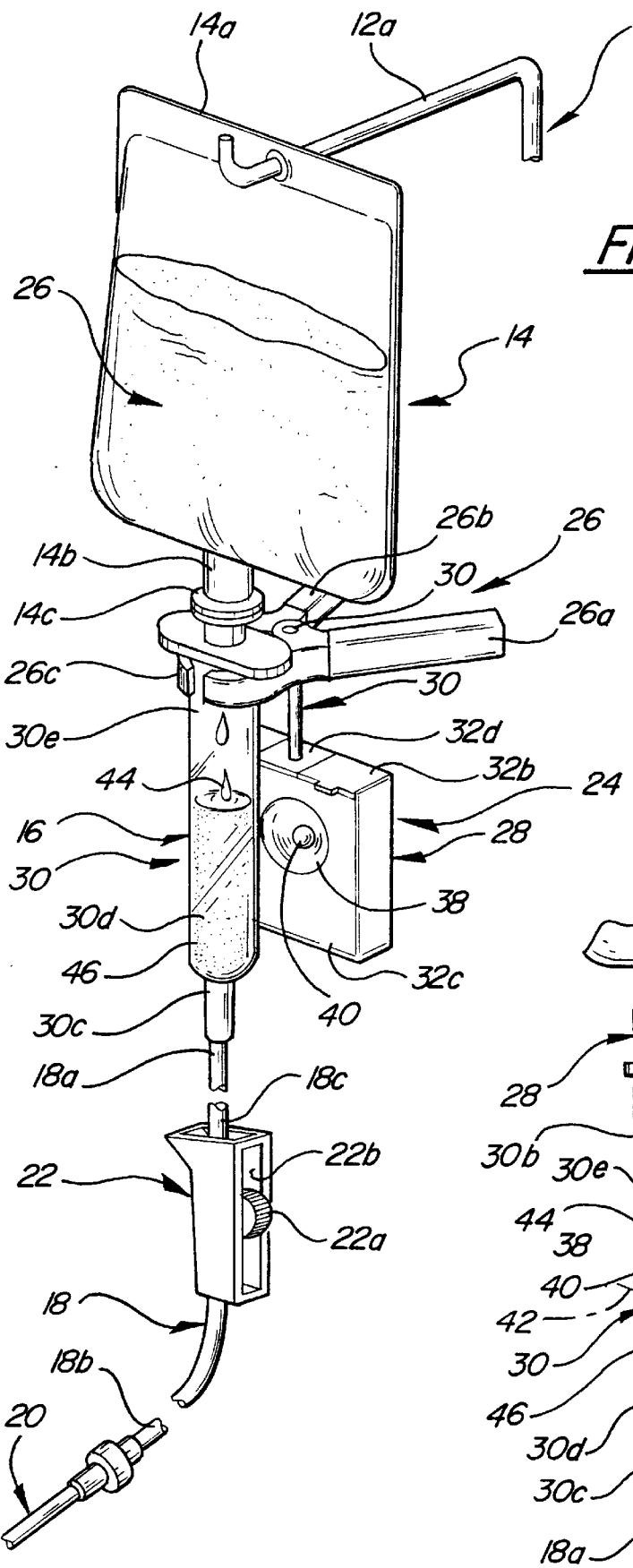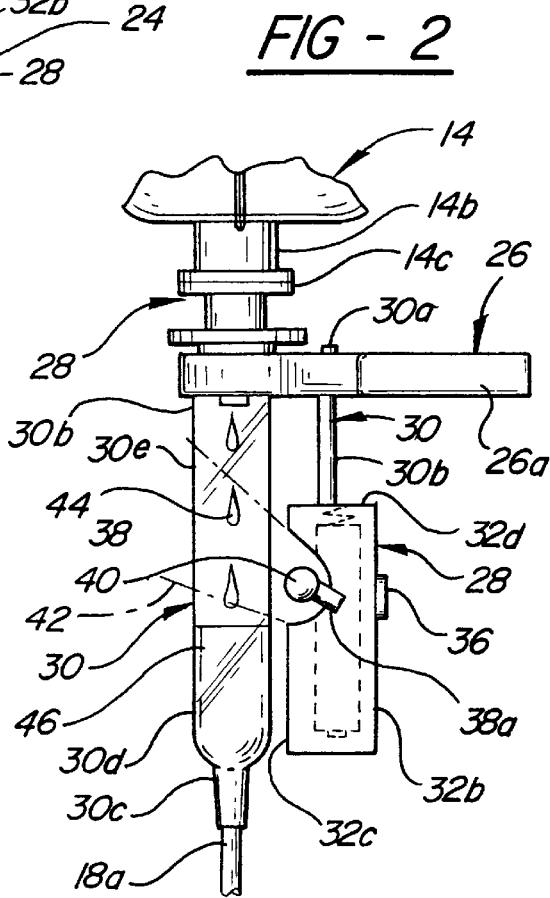

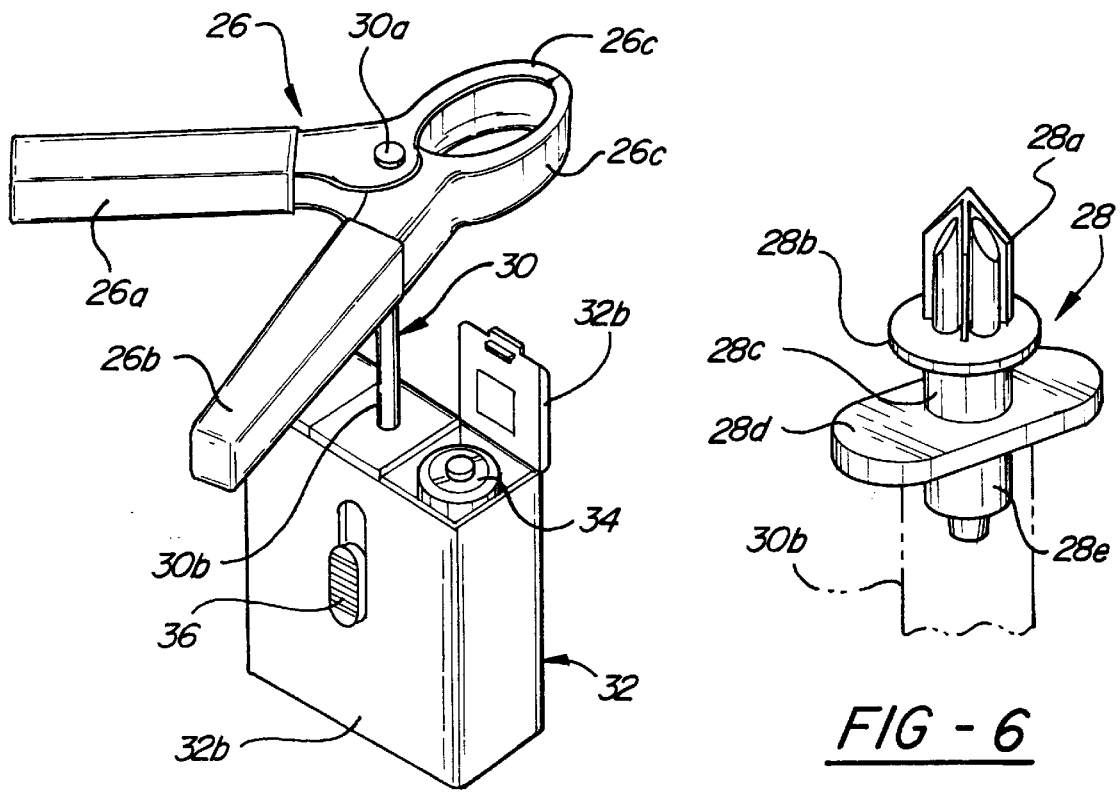
FIG - 3
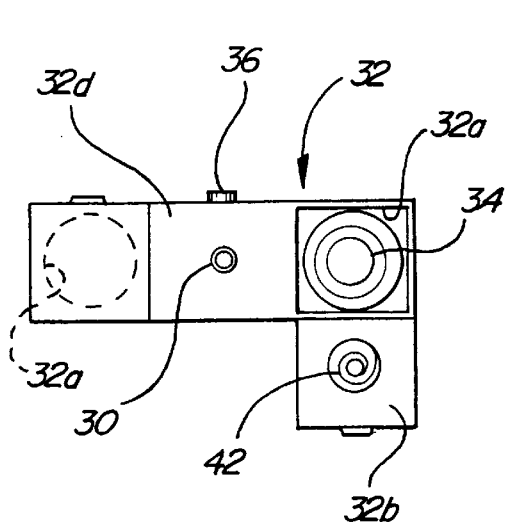
FIG - 4
FIG - 6
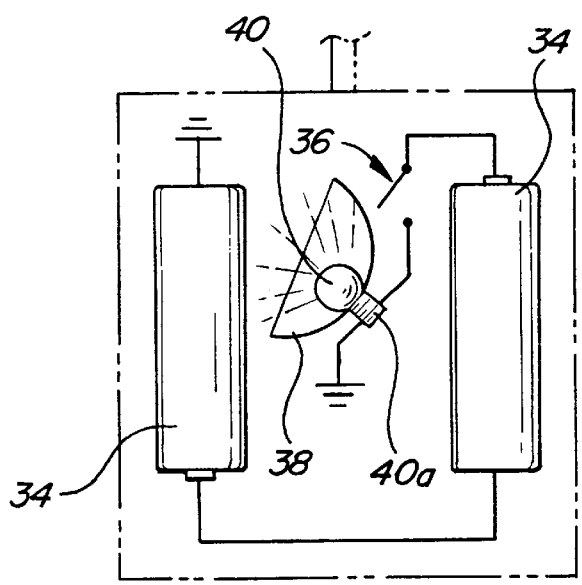
FIG - 5

5,843,045

INFUSION ILLUMINATOR

BACKGROUND OF THE INVENTION

This invention relates to apparatus for the administration of intravenous fluids.

I.V. fluids are generally supplied to a patient under the force of gravity by positioning a container containing the I.V. fluid at an elevated position relative to the patient. The rate of flow is set by a manually adjustable clamp positioned in the line between the bag and the patient. The fluid flows from the reservoir to the patient via a drip chamber attached to the lower, or outlet end of the I.V. bag. The drip chamber includes a drop former which operates to generate discrete, successive drops which fall from the drip former into a reservoir defined at the lower end of the drip chamber from which the fluid flows to the patient via an I.V. delivery tube. The drip chamber is transparent so that the drips may be observed by an anesthesiologist or other medical personnel to insure that drippage is occurring and to further insure that the drippage rate is within appropriate predetermined limits.

It is especially critical that a proper drippage rate be maintained and verified during surgical procedures. However, an increasing number of surgical procedures are being performed in a darkened operating room where the only light is a concentrated, local light at the site of the surgery. Under these conditions, it is virtually impossible to visually determine that drippage is in fact occurring and/or is occurring at the predetermined satisfactory rate.

SUMMARY OF THE INVENTION

This invention is directed to the provision of an improved I.V. apparatus.

More particularly, this invention is directed to the provision of an I.V. apparatus in which the drippage condition of the I.V. fluid may be verified, even under darkened operating room conditions.

The invention relates to an I.V. apparatus of the type including a stand, a bag hangably supported at an upper end thereof from the stand and adapted to contain an I.V. solution, an I.V. tube for intravenous delivery of the I.V. solution to a patient via a catheter, a drip chamber extending downwardly at an upper end thereof from a lower end of the I.V. bag and connected at a lower end thereof with the I.V. tube, and metering means positioned at the lower end of the I.V. bag and operative to deliver I.V. solution in drip fashion from the I.V. bag to the drip chamber.

According to the invention, the apparatus further includes a lamp including a housing, batteries positioned within the housing, a light source positioned in the housing and powered by the batteries, a switch controlling the delivery of power from the batteries to the light source, and means for releasably attaching the lamp to the drip chamber with the housing positioned in freestanding relation to the drip chamber and the light source positioned proximate to but spaced from the drip chamber and operative to illuminate the drip chamber and thereby verify the presence of a drippage flow from the bag to the patient. With this arrangement the anesthesiologist or other medical personnel may readily verify that drippage is in fact occurring and may verify that the drippage is occurring within predetermined limits.

In the disclosed embodiment of the invention, the releasable attaching means comprises a clamp clampingly engaging the upper end of the drip chamber and the lamp further includes a support rod extending downwardly from the clamp and connected at a lower end thereof to the housing. This specific arrangement provides a simple and inexpensive means of providing satisfactory light at the drip chamber.

BRIEF DESCRIPTION OF THE DRAWINGS

FIG. 1 is a perspective view showing an I.V. apparatus including a lamp according to the invention;

FIG. 2 is a detail view of a portion of the I.V. apparatus of FIG. 1;

FIG. 3 is a perspective view of a lamp according to the invention;

FIG. 4 is a top view of a portion of the invention lamp;

FIG. 5 is a circuit diagram of the invention lamp; and

FIG. 6 is a detail view of a portion of the I.V. apparatus.

DETAILED DESCRIPTION OF THE PREFERRED EMBODIMENT

It will be understood that the intravenous apparatus 10 is utilized to administer a parenteral fluid to a patient to maintain a desired condition of the patient during surgery or other medical scenarios.

The I.V. apparatus 10 (FIG. 1) includes a stand 12, a bag 14, a drip chamber 16, a delivery tube 18, a catheter 20, a flow regulator 22, and a lamp assembly 24.

Stand 12 is of known form and includes an upper hook structure 12a adapted to hangingly support the bag 14.

Bag 14 is formed of a suitable transparent plastic material, is hangingly supported at its upper end 14a by hook 12a, contains a desired intravenous fluid such as a saline solution 26, and includes an outlet 14b at the lower end of the bag communicating at its upper end with the interior of the bag and terminating in a lower flange 14c.

Drip chamber 16 includes a plug structure 28 (FIG. 6) and a drip chamber tube structure 30.

Plug structure 28 includes an upper prong structure 28a adapted to be inserted into bag outlet 14b and configured to pierce a diaphragm of the bag in response to such insertion, a flange 28b adapted to be seated against outlet flange 14c in response to insertion of prong 28a into outlet 14b, a tubular central section 28c, a lower flange portion 28d to facilitate the exertion of an upward force on the plug structure to insert 28a into outlet 14b, and a drop former 28e at the lower end of the plug structure.

Drip chamber tube structure 30 is in the form of a cylindrical, transparent plastic tube 30a fitted at its upper end 30b over drop former 28e and defining a nipple 30c positioned beneath a lower portion 30d of the tube structure.

Delivery tube 18 plugs at its upper end 18a into drip chamber nipple 30c and is secured at its lower end 18b to catheter 20.

Catheter 20 is adapted for insertion into a patient body part utilizing a starter needle, in known manner.

Flow regulator 22 is mounted on intermediate portion 18c of delivery tube 18 and includes a wheel 22a moving in a slot 22b and operative in known manner to selectively squeeze delivery tube 18, and thereby control the rate of flow of fluid through the apparatus, in response to selective movement of the wheel within the slot.

Lamp assembly 24 (FIGS. 1–4) includes a clamp 26, a housing assembly 28, and a rod 30.

Clamp 26 includes arms 26a and 26b pivotally mounted on the upper end 30a of rod 30 and each including clamp portion 26c. The arms are biased to a position in which the clamp structures close upon each other by a coil spring (not shown) positioned in surrounding relation to the upper end 30a of rod 30.

Housing assembly 28 includes a housing 32, batteries 34, a switch 36, a reflector 38, and a light source 40.

Housing 32 may, for example, have a hollow plastic configuration and may define left and right vertical battery chambers 32a each accessible at its upper end through a latchable lid structure 32b.

Batteries 34 are of standard size and power and are respectively positioned in chambers 32a with a coil spring 42 mounted on the respective lid 32b maintaining the respective battery in a firm position within the chamber.

Switch 36 is of the slide variety and may be mounted, for example, in a slot in a rear vertical wall 32b of the housing.

Reflector 38 comprises a polished, reflective, metallic bowl-shaped member and may be flush mounted, for example, in a front vertical wall 32c of the housing.

Light source 40 may comprise a light bulb or other source of illumination and may, for example, include a threaded socket 40a threadably received in a threaded reflector socket 38a defined in a central region of the reflector to position the bulb 40b of the light source proximate the focal point of the reflector and allow the reflector to collect and direct light emanating from the bulb and form the collected light into a light beam 42 directed forwardly and upwardly from housing front vertical wall 32c.

The electrical interconnection of the batteries, switch, and light source is shown in FIG. 5 wherein it will be seen that closing of switch 36 in known manner directs power from series-connected batteries 34 to the light source 40 to illuminate the light source.

Rod 30 may be formed of a suitable metallic material. The upper end 30a of the rod defines the pivot axis of the clamp 26 and the lower end 30b of the rod is suitably fixedly secured to the upper wall 32d of the housing.

In the operation of I.V. apparatus 10, drop former 28e operates in known manner to receive solution from bag 26 and form individual, discrete droplets 44 which drop by gravity from the drop former, through an intermediate portion 30e of the drip chamber tube structure, and into a solution reservoir 46 defined in the lower portion 30d of the drip chamber tube structure from where the solution proceeds downwardly and by gravity in known manner through a delivery tube 18 to catheter 20 for infusion into the patient. It is imperative that the presence of a drippage flow from the drop former be constantly verified to insure that infusion at a desired rate into the patient is in fact taking place. This is normally an easy matter for the anesthesiologist or other medical person since the drippage flow in a normally lighted room may be readily observed. However, in situations where the I.V. apparatus is being used in conjunction with surgery taking place in a darkened room with the only light comprising a localized source directed at the site of the surgery, it is impossible to visually verify the presence of the drippage flow or the rate of flow.

In this situation, and according to the invention, lamp assembly 24 is releasably secured to the I.V. apparatus in a manner to illuminate the drip chamber. Specifically, clamp portions 26c of lamp 26 are clampingly secured around the drop former 28e under the urging of the clamp spring so that rod 30 positions housing 24 in freestanding relation to the drip chamber with the light source 40 positioned proximate to but spaced from the intermediate portion 30e of the drip chamber tube structure. Precisely, the light source 40 coacts with reflector 38 to direct light beam 44 forwardly and upwardly from the light source and through the transparent wall of the drip chamber so that the droplets 42, or the absence of droplets, may be readily ascertained and so that the rate of drippage may be readily determined. The length and configuration of rod 30 is of course chosen so as to position the housing assembly 28 relative to the drip chamber such that the beam 44 emanating from the bulb 40/reflector 38 is directed across the intermediate portion of the drip chamber tube structure where the drippage is taking place.

The invention will be seen to provide simple and effective apparatus to enable the drippage flow of an I.V. apparatus to be clearly observed even in situations where the room in which the infusion is taking place is in darkness.

Whereas a preferred embodiment of the invention has been illustrated and described in detail, it will be apparent that various changes may be made in the disclosed embodiment without departing from the scope or spirit of the invention.

I claim:

1. An I.V. apparatus including a support structure, a bag hangingly supported at an upper end thereof from the support structure and adapted to contain an I.V. solution, a delivery tube for intravaneous delivery of the I.V. solution to a patient via a catheter, a drip chamber extending downwardly at an upper end thereof from a lower end of the I.V. bag and connected at a lower end thereof with the delivery tube, and metering means positioned at the lower end of the I.V. bag and operative to deliver I.V. solution in drip fashion from the I.V. bag to the drip chamber:

characterized in that the apparatus further includes a lamp assembly including a single hollow housing, batteries positioned within the housing, a light source positioned in the housing and powered by the batteries, a switch carried by the housing controlling the delivery of power from the batteries to the light source, and an attachment device releasably attaching the housing to the apparatus with the housing positioned in freestanding laterally spaced relation to the drip chamber and the light source positioned proximate to but laterally spaced from the drip chamber and operative to illuminate the drip chamber and thereby enable an attendant to visually observe drops falling downwardly through the drip chamber and thereby verify the presence of a drippage flow from the bag to the patient.

2. An I.V. apparatus including a support structure, a bag hangingly supported at an upper end thereof from the support structure and adapted to contain an I.V. solution, a delivery tube for intravenous delivery of the I.V. solution to a patient via a catheter, a drip chamber extending downwardly at an upper end thereof from a lower end of the I.V. bag and connected at a lower end thereof with the delivery tube, and metering means positioned at the lower end of the I.V. bag and operative to deliver I.V. solution in drip fashion from the I.V. bag to the drip chamber:

characterized in that the apparatus further includes a lamp assembly including a housing, batteries positioned within the housing, a light source positioned in the housing and powered by the batteries, a switch carried by the housing and controlling the delivery of power from the batteries to the light source, and means for releasably attaching the housing to the drip chamber with the housing positioned in freestanding relation to the drip chamber and the light source positioned proximate to but spaced from the drip chamber and operative to illuminate the drip chamber and thereby verify the presence of a drippage flow from the bag to the patient, the releasable attaching means comprising a clamp clampingly engaging the upper end of a drip chamber, the lamp assembly further including a support rod extending downwardly from the clamp and connected at a lower end thereof to the housing.

3. An I.V. apparatus including:

a stand;

a bag hangingly supported at an upper end thereof from the stand and adapted to contain an I.V. solution;

a delivery tube for intravenous delivery of the I.V. solution to a patient via a catheter;

a drip chamber extending downwardly at an upper end thereof from a lower end of the I.V. bag and connected at a lower end thereof with the delivery tube;

metering means positioned at the lower end of the I.V. bag and operative to deliver I.V. solution in drip fashion from the I.V. bag to the drip chamber;

a housing assembly including a single hollow housing, batteries positioned within the housing, a light source positioned in the housing and powered by the batteries, and a switch carried by the housing controlling the delivery of power from the batteries to the light; and means for attaching the housing assembly to the drip chamber with the housing positioned in freestanding laterally spaced relation to the drip chamber and the light source positioned proximate to but laterally spaced from the drip chamber and operative to illuminate the drip chamber and thereby enable an attendant to visually observe drops falling downwardly through the drip chamber and thereby verify the presence of a drippage flow from the bag to the patient.

4. An I.V. apparatus including:

a stand;

a bag hangingly supported at an upper end thereof from the stand and adapted to contain an I.V. solution;

a delivery tube for intravenous delivery of the I.V. solution to a patient via a catheter;

a drip chamber extending downwardly at an upper end thereof from a lower end of the I.V. bag and connected at a lower end thereof with the delivery tube;

metering means positioned at the lower end of the I.V. bag and operative to deliver I.V. solution in drip fashion from the I.V. bag to the drip chamber;

a housing assembly including a housing, batteries positioned within the housing, a light source positioned in the housing and powered by the batteries, and a switch carried by the housing and controlling the delivery of power from the batteries to the light; and means for attaching the housing assembly to the drip chamber with the housing positioned in freestanding relation to the drip chamber and the light source positioned proximate to but spaced from the drip chamber and operative to illuminate the drip chamber and thereby verify the presence of a drippage flow from the bag to the patient, the attaching means comprising a clamp releasably and clampingly engaging the upper end of the drip chamber and a support rod extending downwardly from the clamp and connected at a lower end thereof to the housing.

5. An I.V. apparatus according to claim 4 wherein:

the housing is hollow and defines a front vertically extending wall positioned proximate to but spaced from the drip chamber;

the housing assembly includes a reflector positioned in the front housing wall and opening forwardly; and the light source is positioned in the reflector so that the reflector and light source coact to collect light from the light source and form the collected light into a light beam for direction through an intermediate portion of the drip chamber.

6. A releasable lamp assembly for use with an I.V. apparatus including a support structure, a bag hangingly supported at an upper end thereof from the support structure and adapted to contain an I.V. solution, a delivery tube for intravenous delivery of the I.V. solution to a patient via a catheter, a drip chamber extending downwardly at an upper end thereof from a lower end of the I.V. bag and connected at a lower end thereof to the delivery tube, and metering means positioned at the lower end of the I.V. bag and operative to deliver I.V. solution in drip fashion from the I.V. bag to the drip chamber:

the lamp assembly including a clamp for clampingly and releasably engaging the upper end of the drip chamber, a housing, batteries positioned within the housing, a light source positioned in the housing and powered by the batteries, a switch carried by the housing and controlling the delivery of power from the batteries to the light source, and a support rod extending downwardly from the clamp, connected at a lower end thereof to the housing, and configured, with the clamp clampingly secured to the upper end of the drip chamber, to position the housing in freestanding relation to the drip chamber and position the light source proximate to but spaced from and intermediate portion of the drip chamber whereby to illuminate the intermediate portion of the drip chamber and thereby verify the presence of a drippage flow from the bag to the patient.

7. A lamp assembly according to claim 6 wherein:

the housing is hollow and defines a front vertically extending wall adapted to be positioned proximate but spaced from the drip chamber with the clamp clampingly secured to the upper end of the drip chamber;

the housing assembly includes a reflector positioned in the front housing wall and opening forwardly; and the light source is positioned in the reflector so that the reflector and light source coact to collect light from the light source and form the collected light into a light beam for direction through an intermediate portion of the drip chamber.

* * * * *